(12) United States Patent
Gumiero et al.

(10) Patent No.: US 11,571,157 B2
(45) Date of Patent: Feb. 7, 2023

(54) WEARABLE SENSING DEVICE

(71) Applicant: STMICROELECTRONICS S.r.l., Agrate Brianza (IT)

(72) Inventors: Alessandro Gumiero, Milan (IT); Marco Passoni, Cornate d'Adda (IT); Luigi Della Torre, Lissone (IT); Stefano Rossi, Siena (IT)

( * ) Notice: Subject to any disclaimer, the term of this patent is extended or adjusted under 35 U.S.C. 154(b) by 337 days.

(21) Appl. No.: 16/734,264

(22) Filed: Jan. 3, 2020

(65) Prior Publication Data
US 2020/0221968 A1    Jul. 16, 2020

(30) Foreign Application Priority Data

Jan. 16, 2019   (IT) .................. 102019000000689

(51) Int. Cl.
    *A61B 5/282*      (2021.01)

(52) U.S. Cl.
    CPC ........ *A61B 5/282* (2021.01); *A61B 2562/166* (2013.01); *A61B 2562/227* (2013.01)

(58) Field of Classification Search
CPC ......... A61B 5/282; A61B 5/252; A61B 5/259; A61B 5/274; A61B 5/276; A61B 5/283; A61B 5/285; A61B 5/287; A61B 5/288; A61B 5/29; A61B 5/293; A61B 5/28; A61B 5/25; A61B 5/6833; A61B 5/68335; A61B 5/332; A61B 5/33; A61B 5/333; A61B 2562/166; A61B 2562/227
See application file for complete search history.

(56) References Cited

U.S. PATENT DOCUMENTS

| | | | |
|---|---|---|---|
| 9,277,864 B2 | 3/2016 | Yang et al. | |
| 9,974,444 B2 | 5/2018 | Banet et al. | |
| 2013/0213147 A1* | 8/2013 | Rice ...................... | A43B 7/088 |
| | | | 73/862.046 |
| 2014/0275932 A1 | 9/2014 | Zadig | |
| 2015/0045628 A1 | 2/2015 | Moghadam et al. | |
| 2015/0087948 A1 | 3/2015 | Bishay et al. | |
| 2016/0120433 A1 | 5/2016 | Hughes et al. | |
| 2016/0331257 A1 | 11/2016 | Baumann et al. | |
| 2016/0359150 A1 | 12/2016 | de Francisco Martin et al. | |

(Continued)

FOREIGN PATENT DOCUMENTS

| | | |
|---|---|---|
| CN | 202027572 U | 11/2011 |
| CN | 102525413 A | 7/2012 |

*Primary Examiner* — Tammie K Marlen
(74) *Attorney, Agent, or Firm* — Seed IP Law Group LLP (57) ABSTRACT

A wearable sensing device includes a connector socket provided with contact pads connectable to sensing electrodes for sensing biological electrical signals. A supply module is provided with a battery, which is housed in a first casing configured for reversible coupling with the connector socket. A control module is housed in a second casing distinct from the first casing and configured for coupling with the supply module and with the connector socket. The control module is equipped with a processing unit configured to process biological electrical signals detectable through the contact pads. Mechanical-connection members couple the supply module to the connector socket. Electrical-connection members distinct from the mechanical-connection members are configured to connect the battery and the contact pads to the control module.

22 Claims, 6 Drawing Sheets

(56) References Cited

U.S. PATENT DOCUMENTS

2017/0238833 A1\* 8/2017 Felix ..................... A61B 5/1118
2018/0353110 A1   12/2018 Stafford
2020/0282225 A1\*  9/2020 Kumar .................. A61N 1/046

\* cited by examiner

WEARABLE SENSING DEVICE

BACKGROUND

Technical Field

The present disclosure relates to a wearable sensing device, in particular for long-term monitoring of biological electrical signals.

Description of the Related Art

As is known, long-term biometric monitoring, especially of cardiac signals, has a fundamental importance both for diagnosis of pathological conditions, in particular of the cardiovascular system and for management of situations of potential or current danger for subjects at risk. For instance, constant monitoring of the electrocardiographic (ECG) signal, possibly combined with the measurement of the cardiac rhythm and of respiratory signals, may enable collection of information for sensing significant, albeit not necessarily fatal, events that may occur during everyday activities of the patient and that otherwise might not be observed. In extreme cases, monitoring systems may automatically generate timely alarms and/or requests for immediate help when situations of imminent danger are recognized, such as serious arrhythmias.

Long-term monitoring systems are based upon sensing devices that should be permanently worn by patients, and by a wireless connection that transmits signals thus sensed to the attending physician or even to a surveillance center. For this purpose, sensing devices should be provided with particular characteristics. Firstly, the dimensions should be contained to avoid troubling the patient. Moreover, it should be possible to carry out ordinary operations, such as application, removal, replacement, or recharging of the batteries, in an extremely simple and convenient way, also because very often the patients are elderly persons with limited mobility. Lastly, but by no means less importantly, the batteries should have sufficient autonomy in order not to limit the normal activities of the patient, a fact that may be in contrast with minimizing dimensions and weight. In addition, it would be preferable to use rechargeable batteries rather than disposable ones. There are then other obvious requirements regarding safety and fluid-tightness due to the possible contact with fluids, both body fluids and external fluids, for example when washing or having a shower.

Known devices are not altogether satisfactory, especially in regard to the ease of use in relation to recharging of the batteries. The devices are normally applied using patches provided with electrodes and contacts. Separation of the devices from the patches and subsequent coupling thereto frequently requires a certain amount of force and dexterity that patients do not always possess. Moreover, the pressure to be exerted for coupling the devices to the patches already worn may even be painful.

BRIEF SUMMARY

Embodiments of the present disclosure provide a wearable sensing device that allows overcoming or at least mitigating the limitations described above.

BRIEF DESCRIPTION OF THE SEVERAL VIEWS OF THE DRAWINGS

For a better understanding of the disclosure, some embodiments thereof will now be described purely by way of non-limiting example and with reference to the attached drawings, wherein.

DETAILED DESCRIPTION

Figure 1:
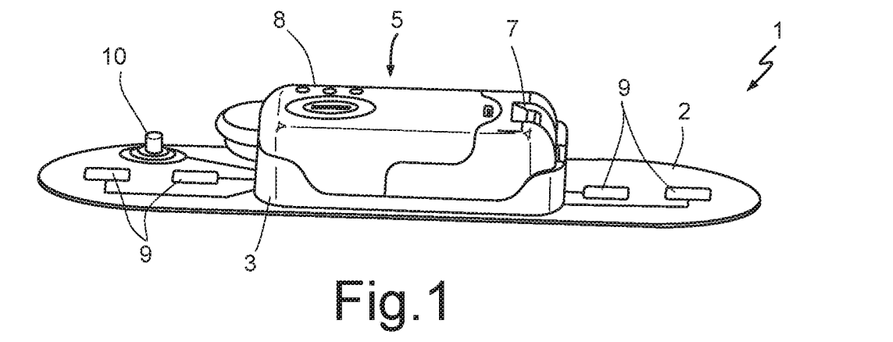
FIG. 1 is an overall perspective view of a wearable sensing device according to an embodiment of the present disclosure.
Figure 2:
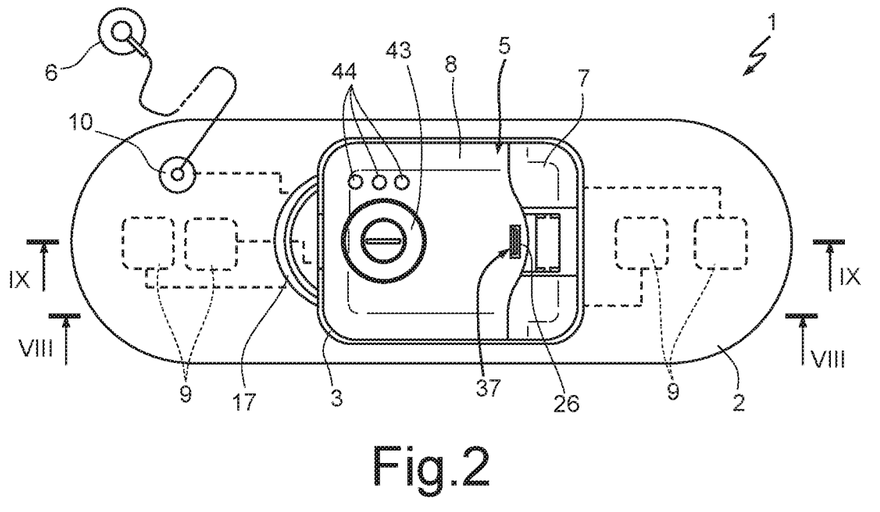
FIG. 2 is a top plan view of the wearable sensing device of FIG. 1.
Figure 3:
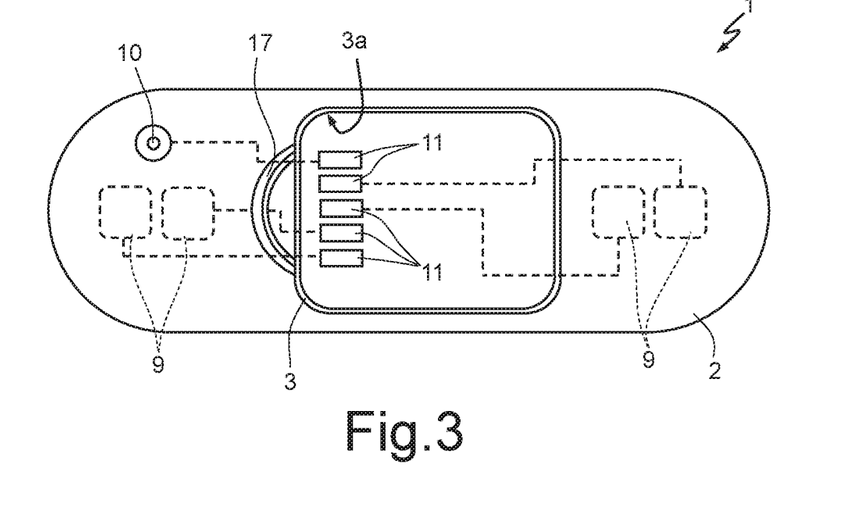
FIG. 3 shows the view of FIG. 2 with a component removed for reasons of clarity.

With reference to FIGS. 1 to 3, number 1 designates as a whole a wearable sensing device for use in a system for long-term monitoring of biological parameters, for example, but not exclusively, electrocardiographic signals. The wearable sensing device 1 comprises a patch 2 that can be applied to the body of a patient, for example to the chest, a connector socket 3, and a sensing assembly 5, in turn including a supply module 7 and a control module 8.

The patch 2 is provided with the electrodes 9 on a surface of the patch 2 itself, which in use is contact with the skin of the patient. A contact 10 is available on the opposite surface of the patch 2 for possible connection, by a connector and wire, of an additional electrode 6, to be applied at a distance from the patch 2. In one embodiment, the contact 10 is configured to provide a releasable connection of the snap-button type. The additional electrode 6 may advantageously be connected to the contact 10 prior to application of the patch 2.

The connector socket 3 is made of polymeric material and has a seat 3a for housing the sensing assembly 5. In one embodiment, the connector socket 3 is permanently fixed to the patch 2 and, as shown in FIG. 3, has contact pads 11 electrically coupled to respective electrodes 9 (one contact pad 11 is coupled to the contact 10).

Figure 8:
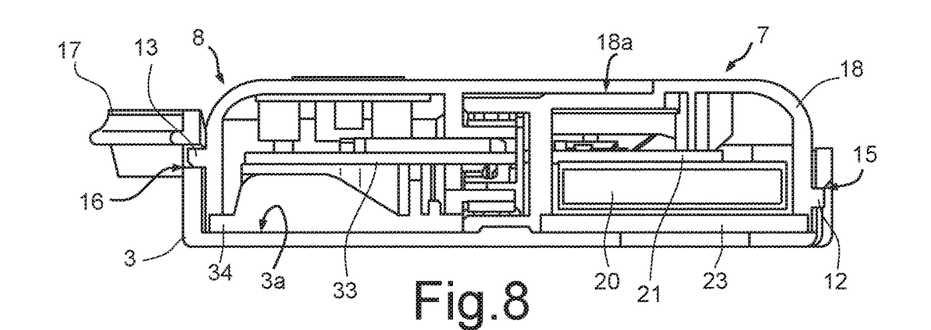
FIG. 8 is a side view of the component of FIG. 4, sectioned along the line VIII-VIII of FIG. 2.

The sensing assembly 5 is inserted, in a removable way, in the connector socket 3 and, as illustrated in FIG. 8, is held in the seat 3a by pivot teeth 12 and blocking teeth 13, which engage, respectively, pivot slots 15 provided on one side of the connector socket 3 and blocking slots 16 provided on an opposite side of the connector socket 3 (see also FIG. 8). A handle 17, on the side of the connector socket 3 where the blocking slots 16 are located, enables bending of the connector socket until the blocking teeth 13 are disengaged from the blocking slots 16. Advantageously, the handle 17 may be provided in the form of an arched portion that extends outwards in a cantilever fashion so that it may be conveniently maneuvered by the patient.

With reference to FIGS. 4 to 9, the supply module 7 and the control module 8 are connected together in a reversible way by a slide coupling and blocking teeth, as described in detail hereinafter.

The supply module 7 (FIG. 7) comprises a shell 18, a battery 20, a printed-circuit board 21, arranged on which is a supply connector 22, and a lid 23, which closes the battery 20 and the printed-circuit board 21 inside the shell 18.

Figure 4:
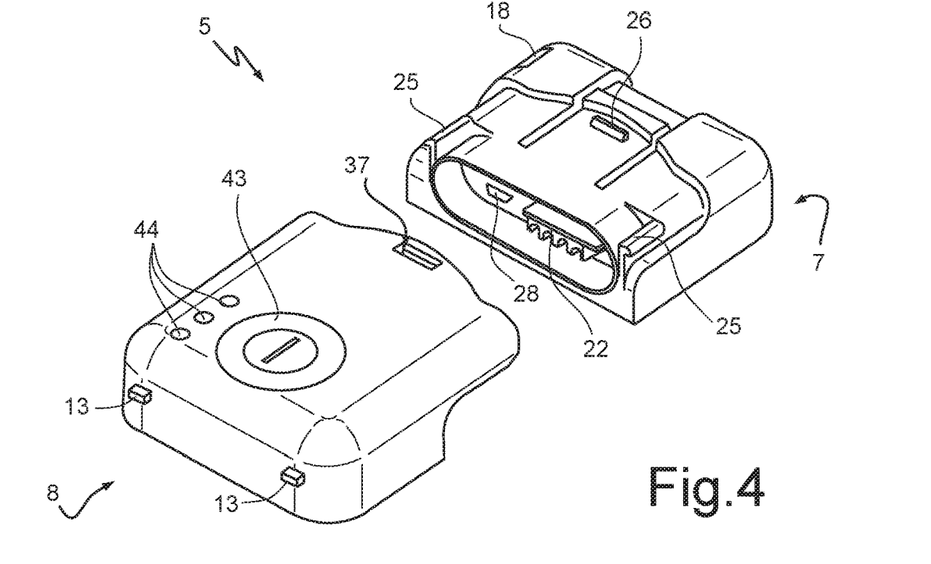
FIG. 4 is a perspective view of a portion of a component of the device of FIG. 1, partially disassembled.
Figure 5:
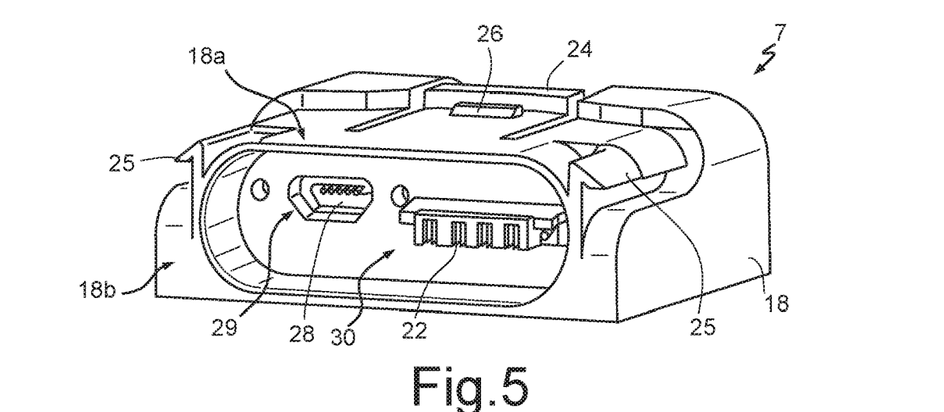
FIG. 5 is a front perspective view of a portion of the component of FIG. 4.

The shell 18 is provided with sliding blocks 25 and a blocking tooth 26 on a face 18a opposite to the connector socket 3 (see also FIGS. 4 and 5). The sliding blocks 25 form coupling members and define a direction of relative sliding of the supply module 7 with respect to the control module 8 in the slide coupling. A portion of the shell 18 where the blocking tooth 26 is located is defined by a tab 24 connected to the rest of the shell 18 on a single side (FIGS. 7 and 9) so that it may be depressed in order to release the blocking tooth 26.

The battery 20 is of a rechargeable type and is connectable to the control module 8 and to an external recharger power supply (not illustrated) respectively through the supply connector 22 on the printed-circuit board 21 and through a recharging connector 28, for example a USB connector. The recharging connector 28 is in turn accessible from the outside of the supply module 7 through a window 29 in the shell 18. In greater detail, the window 29 is provided on a back wall of a recess 30 (FIGS. 4 and 5) formed on a face 18b of the shell 18 that couples to the control module 8. The supply connector 22 projects from the back wall of the recess 30 in the direction of relative sliding of the supply module 7 with respect to the control module 8 in the slide coupling.

The control module 8 comprises (FIG. 7) a shell 32, a printed-circuit board 33, a lid 34, and contacts 35.

The shell 32 comprises a housing 32a, in which the printed-circuit board 33 is arranged, and a connection plate 32b, which extends from the housing 32a and is configured to couple with the supply module 7. In greater detail, the connection plate 32b is provided with rectilinear guides 36 (FIG. 6), which are engaged in a slidable way by the sliding blocks 25 and covers a portion of the face 18a of the shell 18 of the supply module 7, when the supply module 7 and the control module 8 are coupled together. The connection plate 32b is moreover provided with a blocking slot 37, which is engaged by the blocking tooth 26 of the supply module 7, when the control module 8 and the supply module 7 are coupled together.

Figure 6:
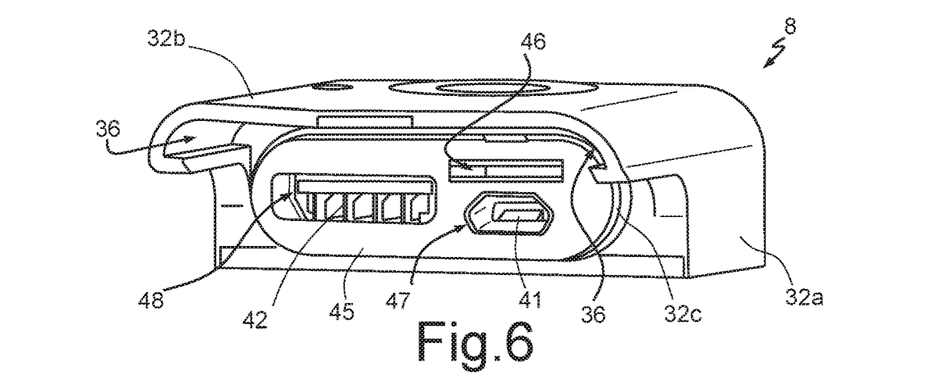
FIG. 6 is a rear perspective view of a second portion of the component of FIG. 4.
Figure 7:
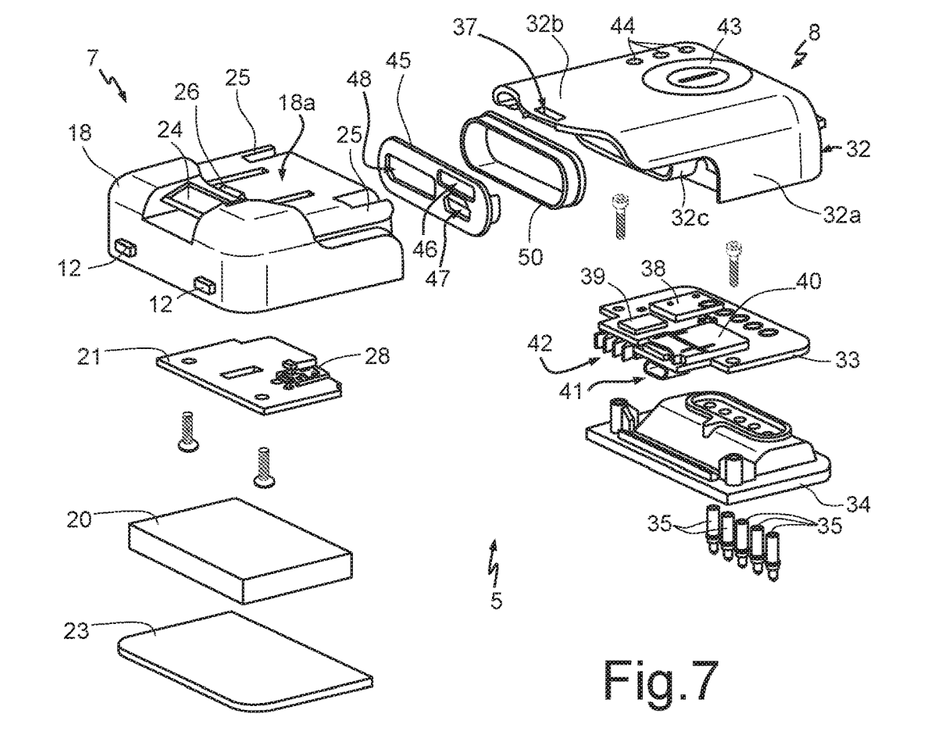
FIG. 7 is an exploded perspective view of the component of FIG. 4.

A protrusion 32c on a face of the shell 32 that couples to the supply module 7 is shaped so as to engage the recess 30 provided in the shell 18 and is hollow (FIGS. 6 and 7).

Arranged on the printed-circuit board 33 are a processing circuit or unit, such as a microprocessor 38, a movement sensor 39, a housing 40 for a memory card, and a communication connector 41, for example, a USB connector. Moreover, provided on the printed-circuit board 33 is a supply connector 42 configured to be reversibly coupled to the supply connector 22 of the supply module 7. In practice, the supply connector 42 of the control module 8 receives the supply connector 22 of the supply module 7 when the protrusion 32c is inserted into the recess 30.

The microprocessor 38 is configured to process and store in the memory card inserted in the housing 40 the signals received through the contacts 35 and from the movement sensor 39, which advantageously may be a microelectromechanical accelerometer or gyroscope. In particular, the microprocessor 38 executes preliminary operations, such as filtering and sampling of the signals received from the contacts 35, to obtain, in the embodiment described, different leads of the electrocardiographic signal. Furthermore, the microprocessor 38 may be configured to: process the ECG signal for extracting information on the cardiac rhythm and on possible anomalies, such as arrhythmias of various degrees of seriousness; correlate the ECG signal with the signals coming from the movement sensor 39 in order to identify anomalous alterations of the cardiac rhythm (for example, an increase in the cardiac rhythm associated with continuous movement may be due to normal physical activity, whereas the absence of movement may be an index of a pathological event in progress); activate emergency procedures, such as warnings or calls to programmed numbers; manage status signals that may be displayed by LED indicators 44 on the shell 32 (such as battery level and possible malfunctioning); and receive commands, for example through a push-button 43 on the shell 32. Advantageously, the microprocessor 38 may be provided with wireless-communication capacity.

The communication connector 41 may be used for connecting the printed-circuit board 33 with an external device (not illustrated), for example for downloading the monitoring data stored in a memory card present in the housing 40.

A flat mask 45 closes the free end of the protrusion 32c of the shell 32 (FIGS. 6-9) and has windows 46, 47, 48 for access to the housing 40, the communication connector 41, and the supply connector 42, respectively. When the battery module 7 and the control module 8 are coupled together, the protrusion 32c engages the recess 30. Consequently, to the advantage of safety, the supply connectors 22, 42, the housing 40, and the communication connector 41 are not accessible when the sensing device 1 is in use. For accessing the supply connectors 22, 42 and the communication connector 41, the battery module 7 has to be separated from the control module 8.

A gasket 50 seals the gap between the side surfaces of the protrusion 32c and of the recess 30, thus preventing fluids from reaching the inside of the battery module 7 and the control module 8 and thus guaranteeing water-tightness.

Figure 9:
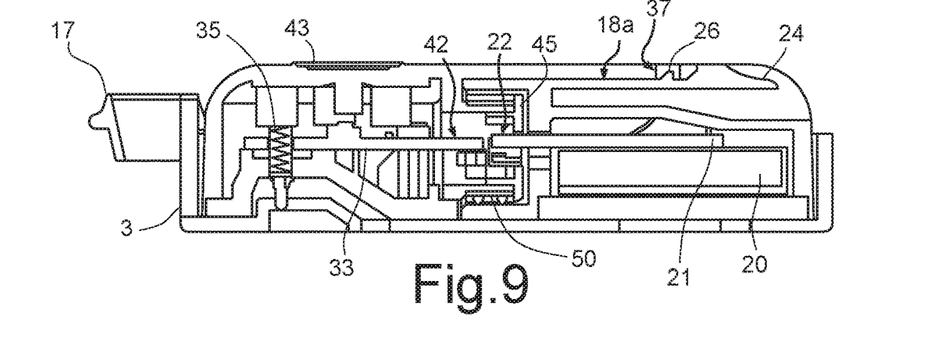
FIG. 9 is a side view of the component of FIG. 4, sectioned along the line IX-IX of FIG. 2.

The contacts 35 are mechanically and electrically coupled to the printed-circuit board 33 and are arranged through the lid 34, which closes the printed-circuit board 33 itself inside the shell 32 (FIG. 9). The contacts 35 are moreover arranged so as to land on respective contact pads 11 of the connector socket 3 when the sensing assembly 5 is in the seat 3a. In one embodiment, the contacts 35 are of the pogo-pin type, with a pin axially slidable within a cylinder between an extracted position and a retracted position against the action of a contrast member that tends to arrange the pin in the extracted position.

The elasticity of the contacts 35 makes it possible to provide a stable coupling with the electrodes 9, 10 without any need to exert significant forces either for making the connection, or for releasing it. In effect, the force to insert and remove the sensing assembly 5 is minimal and is basically determined by the shape of the blocking members (blocking teeth 13 and blocking slots 16) in the seat 3a of the connector socket 3, to the advantage of ease of use. Use of the device is further facilitated by the handle 17, which may be conveniently shaped so as to render insertion and removal of the sensing assembly 5 simple even for patients with motor difficulties.

Likewise, removal of the battery module 7 from the control module 8 is simple and does not require application of significant forces. In practice, provision of two battery modules 7 enables use of the sensing device 1 and replacement and recharging of the batteries in a practically uninterrupted way without any distress for the patient.

With reference to FIGS. 10 to 15, a wearable sensing device 100 according to a different embodiment of the present disclosure comprises a patch 102, a connector socket 103, a supply module 107, and a control module 108.

Figure 10:
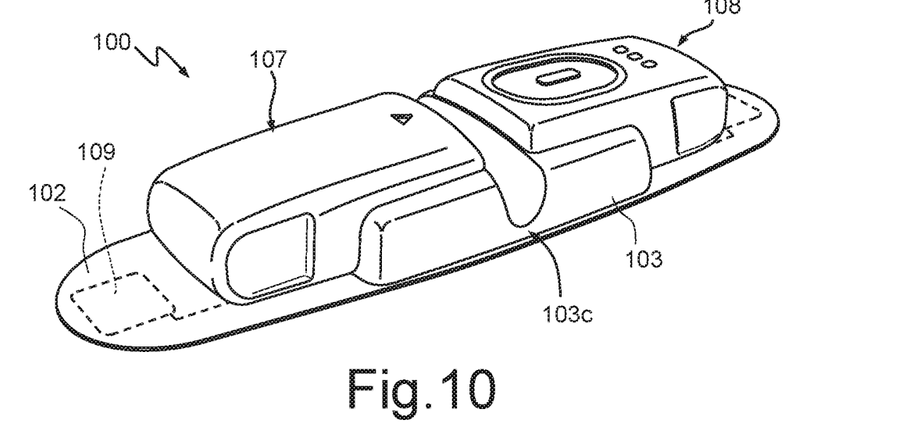
FIG. 10 is an overall perspective view of a wearable sensing device according to a different embodiment of the present disclosure.
Figure 11:
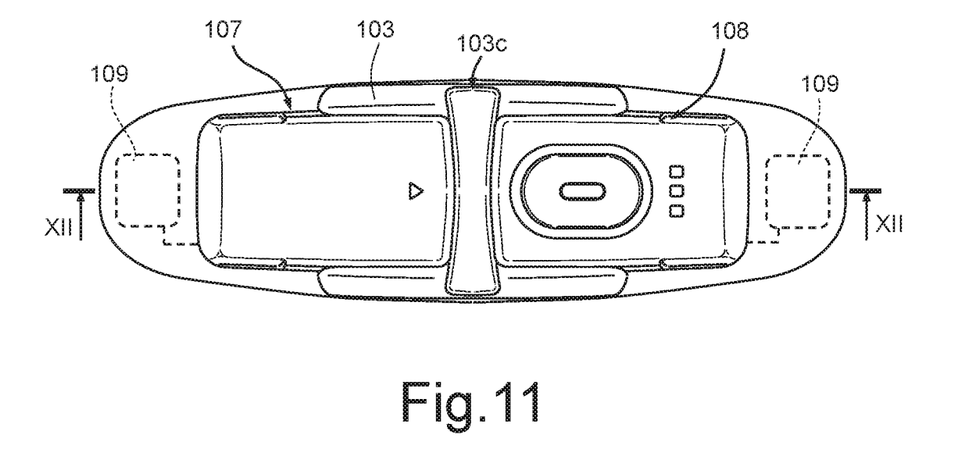
FIG. 11 is a top plan view of the device of FIG. 10.
Figure 12:
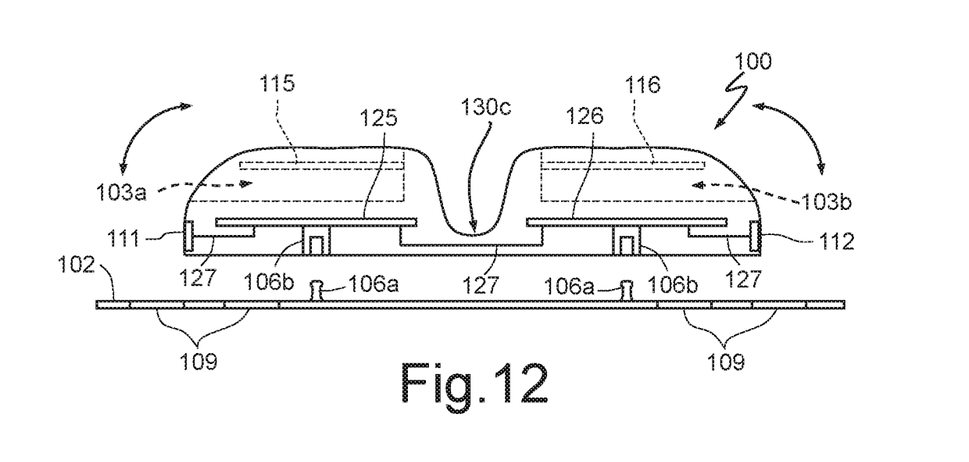
FIG. 12 is a side view of the device of FIG. 10, sectioned along the line XII-XII of FIG. 10, and with parts removed for reasons of clarity.
Figure 13:
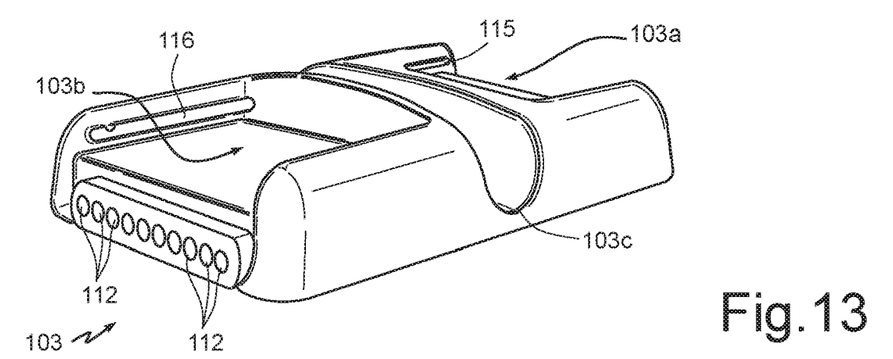
FIG. 13 is a rear perspective view of a first component of the device of FIG. 10.
Figure 14:
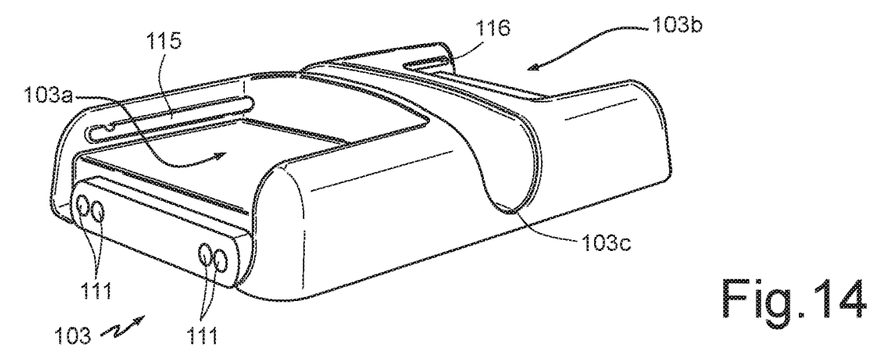
FIG. 14 is a front perspective view of the first component of the device of FIG. 10.
Figure 15:
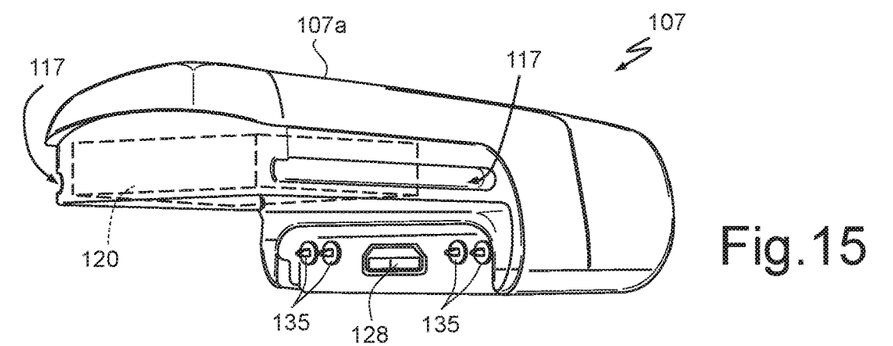
FIG. 15 is a front perspective view of a second component of the device of FIG. 10.

The patch 102 is provided with electrodes 109 for monitoring cardiac activity.

The connector socket 103 may be removably connected to the electrodes 109 of the patch 102, for example by snap-button contacts with pins 106a on the patch 102, and corresponding seats 106b in the connector socket 103 (or vice versa).

Moreover (FIGS. 12 to 14), the connector socket 103 comprises a supply seat 103a and a control seat 103b for receiving, with reversible coupling, the supply module 107 and the control module 108, respectively. The portions of the connector socket 103 that house the supply seat 103a and the control seat 103b are connected together by a joint portion 103c, which enables relative movements so that the sensing device 100 may be adapted to the shape of the patient. The joint portion 103c may function as a hinge and may be made of a single piece of elastic polymeric material together with the portions of the connector socket 103 that house the supply seat 103a and the control seat 103b.

The supply seat 103a and the control seat 103b receive in a reversible way, by slide coupling, the supply module 107 and the control module 108, respectively. For this purpose (FIGS. 12 to 14), the supply seat 103a and the control seat 103b are provided with respective rectilinear guides 115, 116 and respective contact pads 111, 112. The contact pads 111, 112, in particular, are arranged in planes perpendicular to the direction of sliding defined by the rectilinear guides 115, 116.

The seats 106b of the snap-button contacts (FIG. 12) may be provided on printed-circuit boards 125, 126 inside the portions of the connector socket 103 that house the supply seat 103a and the control seat 103b. Connection lines 127 incorporated in the connector socket 103 connect the contact pads 111, on the side of the supply seat 103a, and the seats 106b of the snap-button contacts to the contact pads 112, on the side of the control seat 103b.

The supply module 107 has a slide portion 107a (FIG. 15) provided with rectilinear grooves 117 that are slidingly engaged by the rectilinear guides 115 of the supply seat 103a when the supply module 107 is coupled to the connector socket 103. Moreover, the supply module 107 houses a battery 120 and comprises elastic contacts 135, for example of the pogo-pin type, and a recharging connector 128. The elastic contacts 135 are arranged parallel to the direction of sliding of the slide coupling and land on respective contact pads 111 on the side of the supply seat 103a of the connector socket 103.

Figure 16:
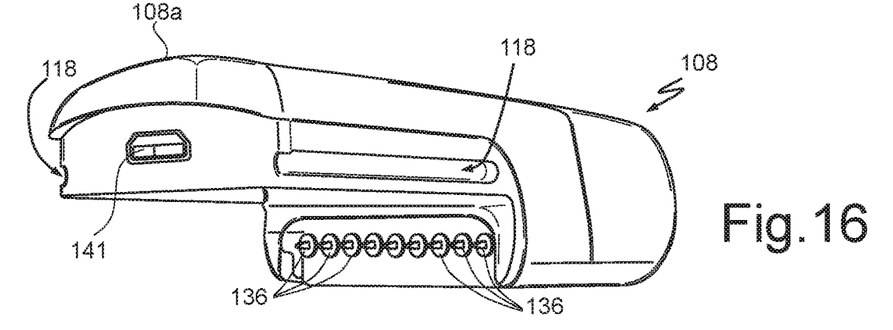
FIG. 16 is a rear perspective view of a third component of the device of FIG. 10.

The supply module 108 has a slide portion 108a (FIG. 16) provided with rectilinear grooves 118, which are slidably engaged by the rectilinear guides 116 of the control seat 103b when the control module 108 is coupled to the connector socket 103. In addition, the control module 108 houses a microprocessor, a memory, and a movement sensor (basically as already described and for this reason not illustrated here) and is provided with elastic contacts 136, for example of the pogo-pin type, and with a communication connector 141. The elastic contacts 136 are arranged parallel to the direction of sliding of the slide coupling and land on respective contact pads 112 on the side of the control seat 103b of the connector socket 103.

Also in this case, the supply module 107 may be easily removed from the connector socket 103 without any need to exert any pressure that might be troublesome for the patient or to detach the patch 102. Coupling of the connector socket to the patch 102 does not create problems, because it may be made before applying the patch 102. Moreover, the sensing device 100 may be applied using an elastic thoracic band instead of a disposable patch.

Coupling between the supply module and the connector socket does not necessarily have to be of the slide type, provided that the elements that hold the supply module in place are distinct from the contacts that establish the electrical connection.

Figure 17:
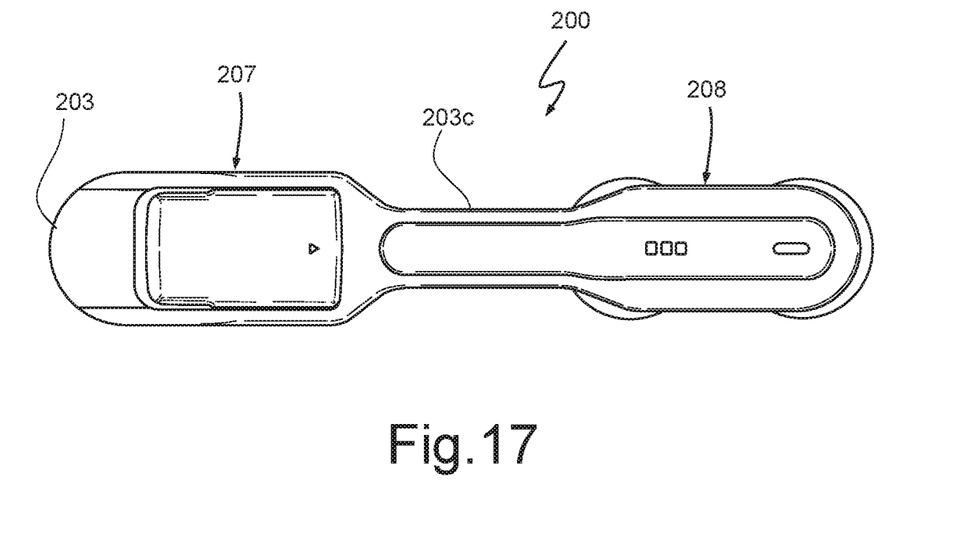
FIG. 17 is a top plan view of a wearable sensing device according to another embodiment of the present disclosure.

According to one embodiment (illustrated in FIG. 17), in a wearable sensing device 200 the control module, here designated by 208, is integrated in the connector socket 203, and the battery module 207 is removable, basically as has already been described. In this case, moreover, the joint portion 203c of the connector socket 203 is lengthened and enables greater relative mobility of the supply module 207 with respect to the control module 208.

Figure 18:
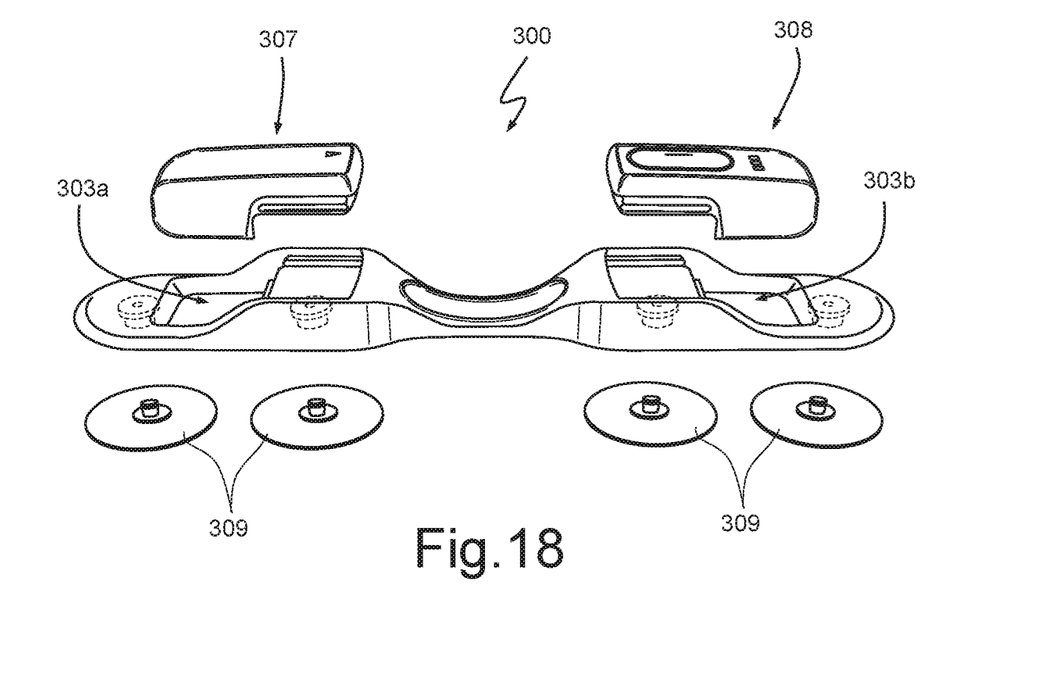
FIG. 18 is an exploded perspective view of a wearable sensing device according to a further different embodiment of the present disclosure.

The same type of joint may obviously be used also when the control module 108 is removable, as in the sensing device 300 according to the embodiment of FIG. 18, where a supply module 307 and a control module 308 are inserted in a removable way in respective seats 303a, 303b of the connector socket 303. In this example, the wearable sensing device, here designated by 300, may be used with conventional ECG electrodes 309, which are less costly than the patch and may be connected to the connector socket 303 before applying them to the patient.

Finally, it is evident that modifications and variations may be made to the electronic device and to the method described herein, without departing from the scope of the present disclosure, as defined in the annexed claims.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A wearable sensing device, comprising:
   a connector socket having contact pads connectable to sensing electrodes configured to sense biological electrical signals;
   a supply module including a battery housed in a first casing, the first casing including mechanical-connection members configured to reversibly couple with the connector socket;
   a control module housed in a second casing distinct from the first casing and configured to couple with the supply module and with the connector socket, the control module including a processing unit configured to process biological electrical signals detectable through the contact pads;

electrical-connection members distinct from the mechanical-connection members and configured to connect the battery and the contact pads to the control module; and pivot teeth on the first casing;

blocking teeth on the second casing;

pivot slots and blocking slots on the connector socket and configured to be engaged by the pivot teeth and by the blocking teeth, respectively, the connector socket having a maneuverable handle configured to disengage the blocking teeth and the blocking slots.

2. The wearable sensing device according to claim 1, comprising a flexible support applicable to a body of a patient and including sensing electrodes, wherein the connector socket is connectable or permanently connected to the flexible support and the contact pads are connectable or permanently connected to respective sensing electrodes.

3. The wearable sensing device according to claim 1, further comprising sensing electrodes applicable to a body of a patient and directly connectable to the connector socket.

4. The wearable sensing device according to claim 1, wherein the supply module and the control module are configured to reversibly mutual couple and form a sensing assembly, and wherein the connector socket has a seat configured to house the sensing assembly.

5. The wearable sensing device according to claim 4, wherein the supply module and the control module are coupled by a slide coupling.

6. The wearable sensing device according to claim 5, wherein the first casing comprises sliding blocks on a face opposite to the connector socket, wherein the second casing comprises a connection plate, extending in a cantilever fashion and having guides that are engagable in a slidable manner by the sliding blocks; and wherein the sliding blocks and the guides define a direction of relative sliding of the supply module with respect to the control module in the slide coupling.

7. The wearable sensing device according to claim 1, wherein the supply module comprises a first printed-circuit board including a first supply connector and a recharging connector configured to connect the battery to the control module and to an external recharger power supply, respectively.

8. The wearable sensing device according to claim 7, wherein the control module comprises a second printed-circuit board including a second supply connector configured to be reversibly coupled to the first supply connector of the supply module.

9. The wearable sensing device according to claim 8, wherein the first supply connector projects towards the control module from a back wall of a recess in a face of the first casing and that couples to the control module, and wherein a face of the second casing that couples to the supply module has a protrusion configured to engage the recess in the first casing, and the recess being hollow.

10. The wearable sensing device according to claim 9, wherein a flat mask closes a free end of the protrusion and has windows configured to provide access to a communication connector and to the second supply connector, respectively.

11. The wearable sensing device according to claim 10, further comprising a gasket that seals a gap between side surfaces of the protrusion and of the recess.

12. The wearable sensing device according to claim 1, wherein the control module comprises elastic contacts arranged to contact the contact pads when the control module is coupled to the connector socket.

13. The wearable sensing device according to claim 1, wherein the control module comprises a movement sensor and wherein the processing unit is configured to identify anomalies in the biological electrical signals received on the basis of correlations with signals supplied by the movement sensor.

14. The wearable sensing device according to claim 1, wherein the connector socket is permanently or reversibly coupled to a patch having sensors for sensing biological electrical signals.

15. A wearable sensing device, comprising:

a connector socket having contact pads connectable to sensing electrodes configured to receive biological electrical signals;

a supply module including:
  a first shell configured to couple with the connector socket; and
  a supply circuit including a battery in the first shell; and
  first electrical connections;

a control module including:
  a second shell distinct from the first shell and configured to couple to the connector socket and the first shell, the second shell being aligned with the connector socket along a first direction while coupled to the connector socket, and aligned with the first shell along a second direction transverse to the first direction while coupled to first shell;
  a control circuit in the second casing shell, the control circuit including a processing circuit configured to process the biological electrical signals on received by the sensing electrodes;
  second electrical connections configured to couple to the first electrical connections, the second electrical connections being aligned with first electrical connections along the second direction while coupled to the first electrical connections, the first and second electrical connections configured to connect the control circuit to the supply circuit; and
  third electrical connections configured to couple to the contact pads, the third electrical connections being aligned with the contact pads along the first direction while coupled to the contact pads.

16. The wearable sensing device of claim 15, wherein the third electrical connections comprise:

a plurality of elastic electrical contacts, each of the plurality of elastic electrical contacts configured to contact a respective one of the contact pads while the second shell is coupled to the first shell.

17. A method, comprising:

connecting contact pads of a connector socket to sensing electrodes configured to sense biological electrical signals;

reversibly coupling mechanical-connection members of a first casing with the connector socket, a supply module including a battery being housed in the first casing;

coupling a control module with the supply module and with the connector socket, the control module being housed in a second casing distinct from the first casing, the control module including a processing circuit configured to process the biological electrical signals detectable through the contact pads;

connecting the battery and the contact pads to the control module, electrical-connection members distinct from the mechanical-connection members connecting the battery and the contact pads to the control module;
engaging pivot slots and blocking slots on the connector socket with pivot teeth on the first casing and blocking teeth on the second casing, respectively; and
disengaging the blocking teeth and the blocking slots with a maneuverable handle of the connector socket.

18. The method of claim 17, wherein coupling the control module with the supply module comprises coupling through a slide coupling the control module and the supply module.

19. A wearable sensing device, comprising:
a connector socket having contact pads connectable to sensing electrodes configured to sense biological electrical signals;
a supply module including a battery housed in a first casing, the first casing including mechanical-connection members configured to reversibly couple with the connector socket, the first casing including sliding blocks on a face opposite to the connector socket;
a control module housed in a second casing distinct from the first casing and configured to couple with the supply module and with the connector socket, the control module including a processing unit configured to process biological electrical signals detectable through the contact pads, the control module configured to couple with the supply module by a slide coupling, the second casing including a connection plate extending in a cantilever fashion and having guides that are engagable in a slidable manner by the sliding blocks, the sliding blocks and the guides define a direction of relative sliding of the supply module with respect to the control module in the slide coupling; and
electrical-connection members distinct from the mechanical-connection members and configured to connect the battery and the contact pads to the control module.

20. The wearable sensing device according to claim 19, further comprising:
a flexible support applicable to a body of a patient and including sensing electrodes, the connector socket being on the flexible support, the contact pads being connected to the sensing electrodes.

21. A wearable sensing device, comprising:
a connector socket having contact pads connectable to sensing electrodes configured to sense biological electrical signals, a supply seat, and a control seat, portions of the connector socket that house the supply seat and the control seat are connected together by a joint portion that enables relative movements between the supply seat and the control seat, the supply seat and the control seat having first rectilinear guides and second rectilinear guides, respectively;
a supply module including a battery housed in a first casing, the first casing including mechanical-connection members configured to reversibly couple with the connector socket, the supply module including a first slide portion having first rectilinear grooves that are slidingly engaged by the first rectilinear guides of the supply seat when the supply module is coupled to the connector socket;
a control module housed in a second casing distinct from the first casing and configured to couple with the supply module and with the connector socket, the control module including a processing unit configured to process biological electrical signals detectable through the contact pads, the supply seat and the control seat configure to receive separately and independently the supply module and the control module, the control module including a second slide portion having second rectilinear grooves that are slidingly engaged by the second rectilinear guides of the control seat when the control module is coupled to the connector socket; and
electrical-connection members distinct from the mechanical-connection members and configured to connect the battery and the contact pads to the control module.

22. The wearable sensing device according to claim 21, wherein first contact pads and second contact pads are arranged in planes perpendicular to a direction of sliding defined by the first rectilinear guides and by the second rectilinear guides.

* * * * *

UNITED STATES PATENT AND TRADEMARK OFFICE
CERTIFICATE OF CORRECTION

PATENT NO. : 11,571,157 B2
APPLICATION NO. : 16/734264
DATED : February 7, 2023
INVENTOR(S) : Alessandro Gumiero et al.

Page 1 of 1

It is certified that error appears in the above-identified patent and that said Letters Patent is hereby corrected as shown below:

In the Claims

Column 8, Line 32, Claim 15:
"second casing shell," should read: --second shell,--.

Signed and Sealed this
Fourteenth Day of March, 2023

Katherine Kelly Vidal
*Director of the United States Patent and Trademark Office*